United States Patent [19]

Argese et al.

[11] Patent Number: 6,150,520

[45] Date of Patent: Nov. 21, 2000

[54] PROCESS FOR THE PREPARATION OF TETRAAZAMACROCYCLES

[75] Inventors: Maria Argese; Giorgio Ripa; Alessandro Scala; Vittorio Valle, all of Milan, Italy

[73] Assignee: Dibra S.p.A., Milan, Italy

[21] Appl. No.: 09/367,221

[22] PCT Filed: Apr. 1, 1998

[86] PCT No.: PCT/EP98/01882

§ 371 Date: Aug. 11, 1999

§ 102(e) Date: Aug. 11, 1999

[87] PCT Pub. No.: WO98/45296

PCT Pub. Date: Oct. 15, 1998

[30] Foreign Application Priority Data

Apr. 4, 1997 [IT] Italy .................................. MI97A0783

[51] Int. Cl.$^7$ ...................... C07D 487/22; C07D 241/00; C07D 235/00

[52] U.S. Cl. ...................... 540/553; 544/343; 548/301.7; 548/302.1

[58] Field of Search ..................... 540/553, 474; 544/343; 548/301.7, 302.1

[56] References Cited

U.S. PATENT DOCUMENTS 3,932,451 1/1976 Bigelow et al. ..................... 260/309.6

FOREIGN PATENT DOCUMENTS

| 42 29 979 A1 | 3/1994 | Germany. |
| 96/28432 | 9/1996 | WIPO. |
| 97/49691 | 12/1997 | WIPO. |

OTHER PUBLICATIONS

Jazwinski et al, "Tricyclic . . . ," Tetrahedron Letters, vol. 22, No. 18, pp. 1711–1714 (1981).

Weisman et al, "Tetracyclic Tetraamines . . . ," Tetrahedron Letters, vol. 21, pp. 335–338 (1980).

*Primary Examiner*—Mukund J. Shah
*Assistant Examiner*—Pavanaram K Sripada
*Attorney, Agent, or Firm*—Nixon & Vanderhye

[57] ABSTRACT

Procedures for preparing compounds of formula (I)

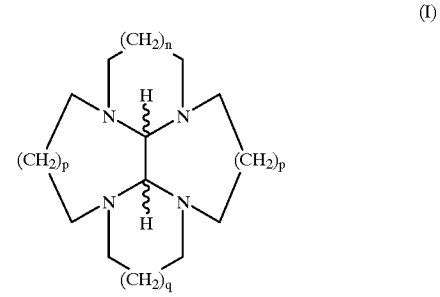

in which n, p and q or independently 0 or 1, are prepared according to the reaction scheme:

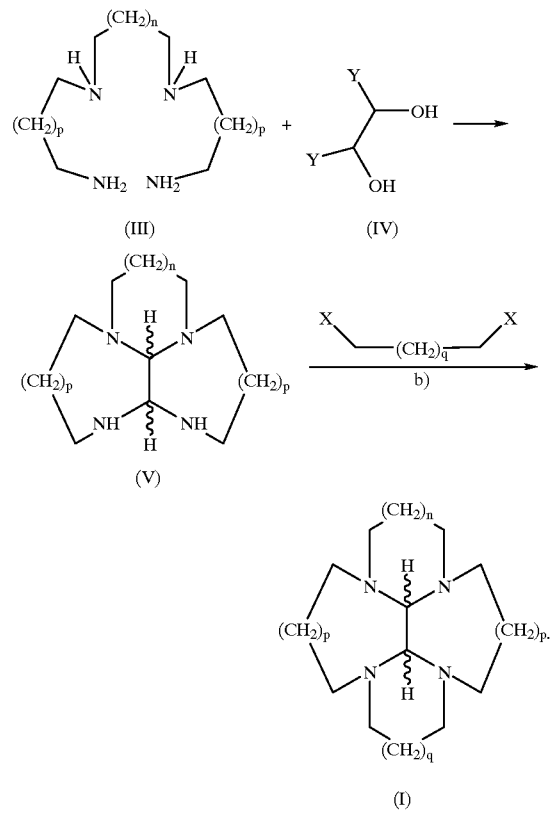

6 Claims, No Drawings

PROCESS FOR THE PREPARATION OF TETRAAZAMACROCYCLES

This is a 35 U.S.C. § 371 of PCT/EP98/01882, filed Apr. 1, 1998.

The present invention relates to a process for the synthesis of compounds of general formula (I), useful intermediates for the synthesis of tetraazamacrocycles of general formula (II)

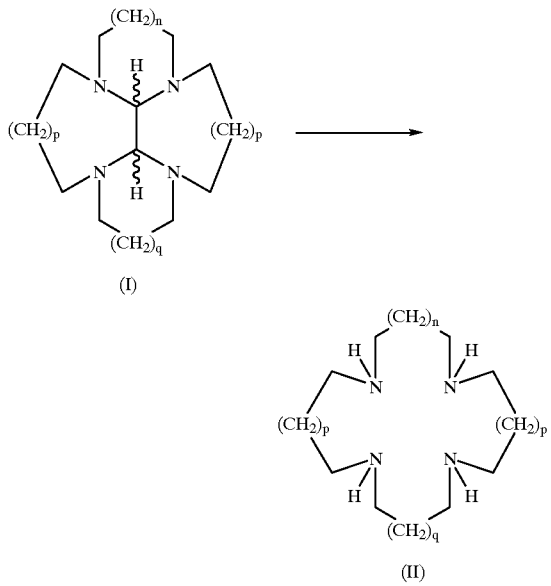

in which n, p and q can independently be 0 or 1, comprising the following steps of Scheme 1:

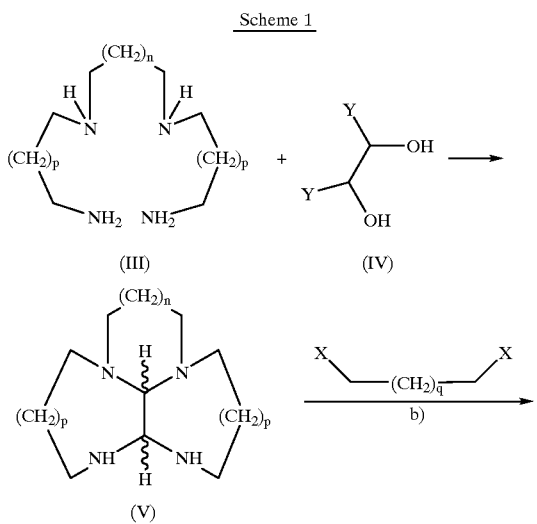

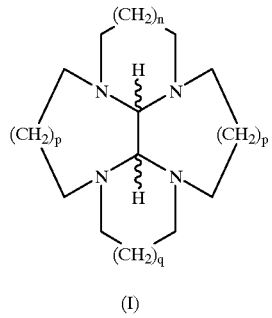

wherein step a): condensation of the polyamine of-formula (III) with the glyoxal derivative of formula (IV), wherein Y is —OH (glyoxal hydrate) or [—$SO_3^-Na^+$] (Bertagnini's salt), in water or in water-soluble solvents or in mixtures thereof, at a temperature of 0–50° C., in the presence of stoichiometric amounts or of a slight excess of calcium hydroxide, to give the compound of formula (V);

step b): condensation of the compound of formula (V) with an alkylating agent X—$CH_2$—$(CH_2)_q$—$CH_2$—X, in which q is as previously defined and X is Cl or Br, in ratios of 1 to 5 mols per mol of compound (V), in a dipolar aprotic solvent and in the presence of a base selected from alkali or alkaline-earth metal carbonates, in ratios of 5 to 10 mols per mol of compound (V), and with the addition of NaZ, wherein Z is I or Br, as catalyst in ratios of 0.1 to 2 mols per mol of compound (V), wherein X and Z are not at the same time Br, at a temperature from 25 to 150° C., to give compound of formula (I).

The compounds of general formula (I) are important intermediates for the synthesis of tetraazamacrocycles of formula (II) according to the steps illustrated in Scheme 2, as already described in Italian Patent application MI 96A001257 and exemplified in the Experimental Section of the present Patent:

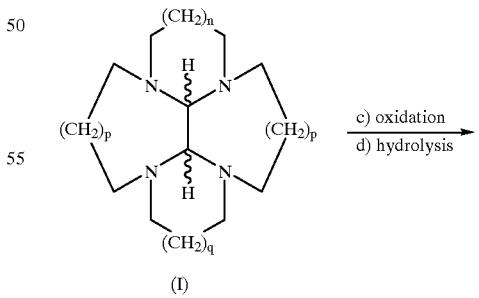

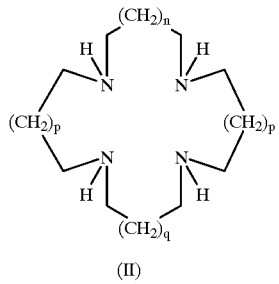

(II)

wherein step c): oxidation of the compound of formula (II) with an oxidizing agent suitable for the aliphatic amines, in water or in a diphasic system consisting of water and an organic solvent, resistant to oxidative conditions, at a temperature of 0–100° C., to give a mixture of oxidized products which is subjected directly to step d): hydrolysis in acid aqueous medium at pH lower than 2 or in basic aqueous medium at pH higher than 12, at a temperature of 110–200° C., to give the compound of formula (II).

The process of the present invention is particularly preferred for the preparation of decahydro-2a,4a,6a,8a-tetraazacyclopent[fg]acenaphthylene of formula (VI), an useful intermediate for the synthesis of 1,4,7,10-tetraazacyclododecane of formula (VII),

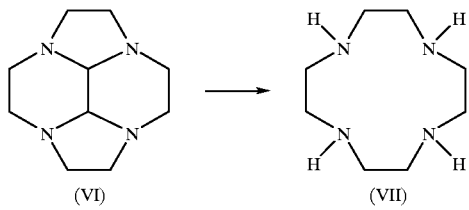

which corresponds to the case in which in the compound of formula (I) n, p and q are 0.

1,4,7,10-Tetraazacyclododecane (commonly known as Cyclen) is the precursor for the synthesis of macrocyclic chelating agents for metal ions, as these chelating agents form very stable complexes with such ions.

In particular, the complexes with the paramagnetic metal ions, specifically the gadolinium ion, of said chelates can be used in the medical diagnostic field through Nuclear Magnetic Resonance technique, otherwise troublesome due to the high toxicity of the free ion.

At present, two contrast media are commercially available, namely Dotarem(®) and Prohance(®), two gadolinium complexes the chemical structure of which is based on Cyclen, while others are still under investigation. Therefore, it is important to work out a synthetic process for the preparation of said "building block", which is cost-saving and industrially advantageous.

It has surprisingly been found, and this is the object of the present invention, that the addition of NaZ in the step of formation of the compound of formula (I) starting from the intermediate of formula (V), remarkably improves yields, as evidenced in the Experimental section.

Particularly preferred is the use of 1,2-dichloroethane as (C-2)-alkylating agent, in addition to the use of NaBr as catalyst. This reactive combination turned out to be extremely advantageous both from an economical (increase in yields, low cost of the starting materials), and environmental point of view.

In particular, the improvement in yields, compared with the cases involving the use of only 1,2-dichloroethane or of only 1,2-dibromoethane, may be explained in terms of reactivity. 1,2-Dichloroethane is, in fact, not very reactive, whereas 1,2-dibromoethane is very reactive towards the intermediate (V): therefore, the reaction of 1,2-dichloroethane is generally slow, even at a high temperature (80° C.), whereas that of 1,2-dibromoethane is rapid and difficult to control even at intermediate temperatures (50° C.), mainly due to side-reactions, which can involve the quaternization of the nitrogen atoms.

The system consisting of 1,2-dichloroethane plus NaBr permits to increase the selectivity with respect to the main reaction, in that it allows to produce in situ the alkylating agent which is reactive enough for cyclization, but not for side-reactions, to take place. In substance, the alkylating agent is present in the reaction mixture in a concentration whose reactivity never involves triggering of the side reactions. Likewise efficient proved to be the system consisting of 1,2-dibromoethane and NaI, at a temperature lower than that used to carry out the reaction using only 1,2-dibromoethane as reagent.

The alkylating agent is generally used in ratios of 1 to 5 mols per mol of compound (V).

The reaction takes place in dipolar aprotic solvents, preferably selected from the group consisting of: DMAC (dimethylacetamide), DMF, (dimethylformamide), DMSO (dimethylsulfoxide) and N-methyl-pyrrolidone; and in the presence of an inorganic base, preferably an alkali metal carbonate, in ratios of at least 2 mols per mol of compound (V).

The temperature can range from 25 to 150° C., preferably from 30 to 80° C., depending on the solvent and on the type of alkylating agent. The reaction time is 1–48 h.

In particular, in the case of the combination of 1,2-dichloroethane with NaBr, the temperature ranges from 50 to 80° C. and the reaction time from 2 to 5 h. When using 1,2-dichloroethane and NaI, the temperature ranges from 30 to 50° C. and the reaction time ranges from 5 to 15 h.

Some preparation examples according to the processes of the present invention are herein reported.

EXAMPLE 1

Preparation of 2a,4a,6a,8a-decahydro-tetraazacyclopent[fg]acenaphthylene of Formula (VI)(CAS RN 74199-09-0) Without Addition of Catalyst

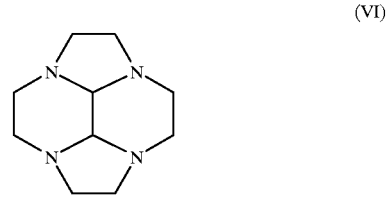

A) Triethylenetetramine hydrate 520 g of commercial triethylenetetramine (62% GC in % area) are dissolved in 800 ml of toluene. 80 ml of water are added under stirring, then the solution is cooled to 25° C. and germinated with purified triethylenetetramine. The suspension is kept under stirring for 45 min. at 20° C., then cooled to 5–10° C. for 1h. The crystallized solid is filtered, washed with few toluene and dried at 30° C. under vacuum for 8 h, to give 365 g of the desired product.

Yield: 91% on theoretical Water content: 17% GC purity: 97% (in % area)

B) 3H,6H-2a,5,6,8a-Octahydro-tetraazacenaphthylene (CAS RN 78695-52-0)

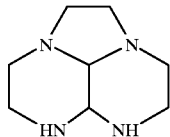

A solution of triethylenetetramine hydrate (100 g, 0.54 mol) in water (1 l) is added with 80 g (1.08 mol) of calcium hydroxide. The milky suspension is cooled to 5° C., then a 5% glyoxal aqueous solution (626 g, 0.54 mol) is added under stirring. After 2 h the reaction is complete (no triethylenetetramine, GC analysis). The solution warmed to 20° C., then the insoluble inorganic solid is filtered off and washed with water. The filtrate is concentrated in rotating evaporator under vacuum to give 100 g of the desired intermediate as a colourless oily liquid.

C) 2a,4a,6a,8a-Decahydro-tetraazacyclopent[fg] acenaphthylene (CAS RN 79236-92-3)

The residue is redissolved in 1 l of DMAC, 101.4 g (0.54 mol) of dibromoethane are added and the resulting solution is added drop by drop to a thoroughly stirred suspension of anhydrous sodium carbonate (600 g) and DMAC (1 l), heated at 100° C. The addition is carried out in 20 min., afterwards the mixture is reacted for a further 30 min. The inorganic salts are filtered off and the filtrate is concentrated in rotating evaporator under vacuum to a residue, which is dissolved in 0.5 l of hexane. Insolubles are filtered off and the filtrate is concentrated to dryness, to give 48 g (0.24 mol) of the desired product.

Yield: 45%

GC: 98.5% (in % area)

EXAMPLE 2

Preparation of the Compound of Formula (VI) Using 1,2-dichloroethane in the Absence of Catalyst and of Solvent

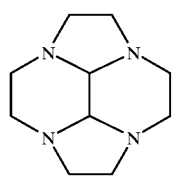

(VI)

80 g (0.48 mol) of 3H,6H-2a,5,6,8a-octahydro-tetraazanaphthylene (prepared as described in Example 1) are dissolved in 0.4 l of 1,2-dichloroethane. 100 g of anhydrous sodium carbonate are added thereto and the suspension is heated to 50° C. for 48 h, then cooled. Insolubles are filtered off and the filtrate is concentrated to dryness. The tetracycle is extracted with 0.4 l of hexane, insolubles are filtered off again and the extract is concentrated to give 31.2 g (0.16 mol) of the tetracycle.

Yield: 33%. GC: 97.5% (in % area)

EXAMPLE 3

Preparation of the Compound of Formula (VI) Using 1.2-dichloroethane in Solvent With the Addition of the Catalyst

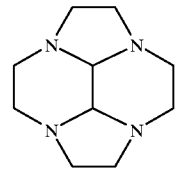

(VI)

266 g (1.58 mol) of 3H,6H-2a,5,6,8a-octahydro-tetraazanaphthylene (prepared as described in Example 1) are added to 4.4 l of dimethylacetamide, 837 g of $Na_2CO_3$ (7.9 mol) and 81.3 g of NaBr (0.79 mol). The suspension is heated to 58° C., then 469 g of 1,2-dichloroethane (4.74 mol) dissolved in 800 ml of DMAC are added under stirring. The mixture is heated to a temperature of 80° C. and reacted for 3 h. The suspension is cooled, salts are filtered off, 192 g of celite are added to the filtrate and solvent is distilled off under reduced pressure. The residue is taken up with hexane and 4 extractions solid-liquid are carried out. The organic extracts are concentrated to dryness to obtain 184 g of the desired product (0.94 mol).

Yield 59%

EXAMPLE 4

Comparison of the Results Obtained With or Without Catalyst, Following the Procedure Described in Example 3

Table 1 summarizes the results obtained following the procedure described in Example 3, using 1,2-dichloroethane as alkylating agent and NaBr as catalyst.

TABLE 1

| | $Cl(CH_2)_2Cl$ (g, mol) | NaBr (g, mol) | T(° C.) | t(h) | yield (%) |
| --- | --- | --- | --- | --- | --- |
| 1 | 469 (4.74) | 162.6 (1.58) | 80 | 2 | 51 |
| 2 | 469 (4.74) | 162.6 (1.58) | 60 | 5 | 54 |
| 3 | 469 (4.74) | 16.26 (0.158) | 80 | 4.5 | 47 |
| 4 | 235 (2.37) | 81.3 (0.79 mol) | 80 | 3 | 45 |
| 5 | 469 (4.74) | | 80 | 5 | 30 |

In the absence of NaBr, the reaction between 3H,6H-2a, 5,6,8a-octahydro-tetraazanaphthylene and 1,2-dichloroethane gives the desired product in a 30% yield (line 5), or in a 33% yield (Example 2), which is lower than both that obtained with 1,2-dibromoethane (Example 1C, 45% yield), and that of the reactions carried out in the presence of NaBr.

The combination 1,2-dichloroethane/NaBr is an alkylation reactant even better than 1,2-dibromoethane itself, in that it attains higher yields. From the industrial point of view, moreover, said combination is advantageous also for economical reasons. The current cost of 1,2-dibromoethane is in fact about 7 times that of 1,2-dichloroethane and twice that of NaBr. With a simple arithmetical calculation, a 72% saving per mol of the desired product can be estimated.

EXAMPLE 5

Preparation of the Compound of Formula (VI) Using NaI as Catalyst

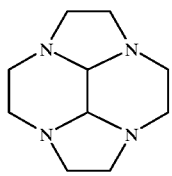
(VI)

Table 2 summarizes the results obtained following the procedure described in Example 3, by reacting 1 mole of 3H,6H-2a,5,6,8a-octahydro-tetraazacenaphthylene (prepared as described in Example 1B) and the alkylating agent X—CH$_2$—CH$_2$—X, wherein X is Cl or Br, in the presence or in the absence of NaI.

TABLE 2

| X | mols | NaI (mol) | T(° C.) | t(h) | yield (%) |
|---|------|-----------|---------|------|-----------|
| Br | 1 | 0 | 100 | 1 | 45 |
| Br | 1 | 0 | 50 | 5 | 40 |
| Br | 1 | 0 | 30 | 12 | 38 |
| Br | 1.2 | 0.2 | 30 | 12 | 45 |
| Br | 1.2 | 0.5 | 30 | 5 | 52 |
| Cl | 3.0 | 0 | 80 | 5 | 30 |
| Cl | 3.0 | 0.5 | 50 | 5 | 56 |
| Cl | 3.0 | 1.0 | 50 | 5 | 49 |
| Cl | 3.0 | 1.0 | 30 | 12 | 42 |
| Cl | 3.0 | 2.0 | 30 | 12 | 51 |

EXAMPLE 6

Preparation of 1,4,7,10-tetraazacyclododecane of Formula (VII)

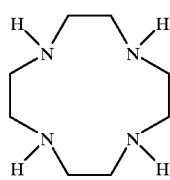
(VII)

50.4 g (0.259 mol) of 2a,4a,6a,8a-decahydro-tetraazacyclopent[fg]acenaphthylene (obtained according to the procedure described in Examples 1, 2), are dissolved in 455 g of deionized water. 557.5 g of 1N HCl are added to pH 4.5, then the solution is cooled to a temperature of 20° C. and 104.4 g of Br$_2$ (0.651 mol) and 1.42 kg of 1N NaOH are added drop by drop therein, at the same time, to keep pH at 4.5.

After reacting overnight at room temperature, 258.91 g of NaOH in pellets are added up to pH 14, then the solution is placed into autoclave and hydrolyzed at 180–185° C. for 5.5 h. After cooling to room temperature, the solution is concentrated under reduced pressure. The resulting suspension is kept under stirring at room temperature for 24 h, then the precipitate is filtered. The wet solid is dried in a vacuum-oven, to obtain 1,4,7,10-tetraazacyclododecane contaminated by inorganic salts. The solid is suspended in 400 g of toluene and refluxed, removing azeotropically water and reintegrating with fresh toluene. The inorganic salts are removed by filtering the hot mixture, and washed with pre-heated toluene. The filtrate is concentrated to 50 ml, then cooled to 17° C. for 2 h and to 0° C. for 1 h. The crystallized solid is filtered, washed with some toluene and the product is dried at 50° C. under vacuum, to give 24.3 g of the desired product, of good purity (99.23%, GC).

Total yield: 54%.

What is claimed is:

1. A process for the preparation of compounds of formula (I)

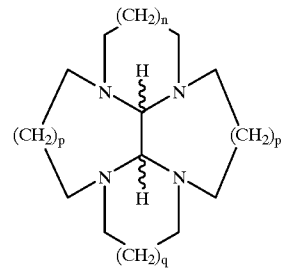
(I)

in which n, p and q can independently be 0 or 1, comprising the following steps according to the Scheme:

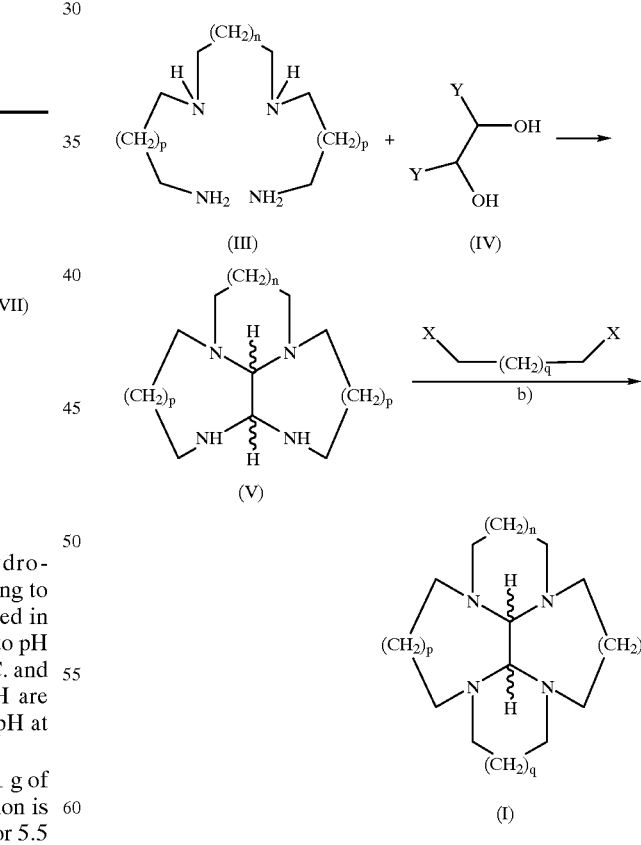

wherein step a): condensation of the polyamine of formula (III) with the glyoxal derivative of formula (IV), wherein Y is —OH (glyoxal hydrate) or [—SO$_3^-$Na$^{+}$] (Bertagnini's salt), in water or in water-soluble solvents or in mixtures thereof, at a temperature of 0 to 50° C., in the presence of stoichiometric amounts or of a slight excess of calcium hydroxide, to give the compound of formula (V);

step b): condensation of the compound of formula (V) with an alkylating agent X—$CH_2$—$(CH_2)_q$—$CH_2$—X, in which q is as previously defined and X is Cl or Br, in ratios of 1 to 5 mols per mol of compound (V), in a dipolar aprotic solvent and in the presence of a base selected from alkali or alkaline-earth metal carbonates, in ratios of 5 to 10 mols per mol of compound (V), and with the addition of NaZ, wherein Z is I or Br, as catalyst in ratios of 0.1 to 2 mols per mol of compound (V), wherein X and Z are not at the same time Br, at a temperature from 25 to 150° C., to give the compound of formula (I).

2. A process according to claim 1, wherein in the compound of formula (I), n, p and q are 0.

3. A process according to claim 1, wherein compound X is Cl and Z is Br.

4. A process according to claim 3, wherein the dipolar aprotic solvent is selected from dimethylacetamide dimethylformamide, dimethylsulfoxide, N-methylpyrrolidone, in the presence of a base selected from alkali metal carbonates in ratios of at least 2 mols of base per mol of compound (V), the alkylating agent being in ratios of 1 to 5 mol per mol of compound (V), the temperature ranging from 50 to 80° C. and the reaction time ranging from 2 to 5 hours.

5. A process according to claim 1, wherein X is Cl and Z is I.

6. A process according to claim 5, wherein the dipolar aprotic solvent is selected from dimethylacetamide, dimethylformamide, dimethylsulfoxide, N-methylpyrrolidone, in the presence of a base selected from alkali metal carbonates in a ratio of at least 2 mols per mol of compound (V), the alkylating agent being in ratios of 1 to 5 mols per mol of compound, the temperature ranging from 30 to 50° C. and the reaction time ranging from 5 to 15 hours.

* * * * *